United States Patent
Gendronneau et al.

(10) Patent No.: US 10,745,755 B2
(45) Date of Patent: Aug. 18, 2020

(54) SESTRIN ACTIVATORS FOR PREVENTING AND/OR ATTENUATING SKIN AGEING AND/OR HYDRATING THE SKIN AND/OR FOR REGULATING SKIN PIGMENTATION

(71) Applicant: CHANEL PARFUMS BEAUTE, Neuilly sur Seine (FR)

(72) Inventors: Gaelle Gendronneau, Chaumes-en-brie (FR); Irina Berlin, Paris (FR); Francois Lejeune, Andeville (FR); Julie Latreille, Paris (FR)

(73) Assignee: CHANEL PARFUMS BEAUTE, Neuilly Sur Seine (FR)

( * ) Notice: Subject to any disclaimer, the term of this patent is extended or adjusted under 35 U.S.C. 154(b) by 107 days.

(21) Appl. No.: 15/511,129

(22) PCT Filed: Sep. 25, 2015

(86) PCT No.: PCT/EP2015/072080
§ 371 (c)(1),
(2) Date: Mar. 14, 2017

(87) PCT Pub. No.: WO2016/046358
PCT Pub. Date: Mar. 31, 2016

(65) Prior Publication Data
US 2017/0275694 A1 Sep. 28, 2017

(30) Foreign Application Priority Data

Sep. 26, 2014 (EP) ..................................... 14306505

(51) Int. Cl.
*C12Q 1/68* (2018.01)
*C12Q 1/6883* (2018.01)

(52) U.S. Cl.
CPC ............ *C12Q 1/6883* (2013.01); *C12Q 1/68* (2013.01); *C12Q 2600/148* (2013.01); *C12Q 2600/158* (2013.01)

(58) Field of Classification Search
None
See application file for complete search history.

(56) References Cited

U.S. PATENT DOCUMENTS

2015/0017269 A1* 1/2015 Fournial ................ A61Q 19/08
424/756

FOREIGN PATENT DOCUMENTS

JP 2003-048812 2/2003
WO WO 2012/156419 11/2012

OTHER PUBLICATIONS

Zhao et al., Journal of Biological Chemistry, vol. 289, No. 52, pp. 35806-35814, 2014.*
Zaidi et al. (Mini-reviews in Medicinal Chemistry, 2019, vol. 19, pp. 796-808).*
International Search Report, PCT/EP2015/072080, dated Nov. 16, 2015.
Raymond L Warters et al: "Differential gene expression in primary human skin keratinocytes and fibroblasts in response to ionizing radiation", Radiation Research, Academic Press Inc, US, vol. 172, No. 1, Jul. 1, 2009 (Jul. 1, 2009), pp. 82-95, XP002638907, ISSN: 0033-7587, DOI: 10.1667/RR1677.1 p. 86, figure 2—, abstract.
Yevgeniya A Byekova et al: "Liver kinase B1 (LKB1) in the pathogenesis of UVB-induced murine basal cell carcinoma". Archives of Biochemistry and Biophysics. vo 1. 508. No. 2. Jan. 25, 2011 (Jan. 25, 2011). pp. 204-211. XP028367324, ISSN: 0003-9861, DOI: 10.1016/J.ABB.2011.01.006 [retrieved on Jan. 25, 2011] p. 206. last paragraph—p. 207.
Budanov A V et al: "Identification of a novel stress-responsive gene Hi95 involved in regulation of cell viability". Oncogene. Nature Publishing Group. GB. vol. 21. Jan. 1, 2002 (Jan. 1, 2002), pp. 6017-6031. XP003017166, ISSN: 0950-9232. DOI: 10.1038/SJ.ONC.1205877.
B. Zhao et al: "Sestrin2 Protein Positively Regulates AKI Enzyme Signaling and Survival in Human Squamous Cell Carcinoma and Melanoma Cells", Journal of Biological Chemistry. vol. 289. No. 52, Nov. 6, 2014 (Nov. 6, 2014), pages.

* cited by examiner

*Primary Examiner* — Celine X Qian
(74) *Attorney, Agent, or Firm* — Young & Thompson

(57) ABSTRACT

The disclosure relates to the identification and the use of compounds which regulate the expression of at least one Sestrin gene, for preventing and/or attenuating skin ageing, and/or for hydrating the skin and/or for regulating skin pigmentation. The method includes the following steps: a. bringing at least one test compound in contact with a sample of human keratinocytes or melanocytes; b. measuring the expression of at least one Sestrin gene chosen from SESN3, SESN2 and SESN1 in the keratinocytes or melanocytes; c. selecting the compounds for which an activation of at least 1.6 fold of the expression of at least one of the genes is measured in the keratinocytes treated in a. compared with the untreated keratinocytes, or for which a significant modulation of the expression of at least one of the genes is measured in the melanocytes treated in a. compared with the untreated melanocytes.

5 Claims, No Drawings

SESTRIN ACTIVATORS FOR PREVENTING AND/OR ATTENUATING SKIN AGEING AND/OR HYDRATING THE SKIN AND/OR FOR REGULATING SKIN PIGMENTATION

The invention relates to a method for identifying compounds which regulate the expression of at least one gene selected from SESN1, SESN2 and SESN3, for preventing and/or attenuating skin ageing, particularly photo-ageing, and/or for hydrating the skin, and/or for regulating skin pigmentation.

Sestrins (SESN) are recently identified proteins, highly conserved throughout the animal kingdom. Three SESN genes have been identified in mammals, SESN1, SESN2 and SESN3 that encode for variant proteins produced by alternative splicing.

Sestrins were first discovered as genotoxic and/or oxidative stress-inducible genes, notably implicated in the regulation of redox status (Velasco-Miguel et al, 1999, Oncogene; Budanov et al, 2002, Oncogene; Chen et al, 2010, Dev. Cell). In response to stress, SESN1 and SESN2 expression is induced in a p53-dependent manner, while Sesn3 expression is preferentially induced by FoxO transcription factors in human cell lines. All three SESN members have been shown to reduce intracellular reactive oxygen species (Kopnin et al, 2007, Cancer Res), probably by acting on peroxiredoxins regeneration (Budanov et al, 2004, Science). In human reconstructed skin, Sestrins expression is modulated after UV daylight exposure (Marionnet et al, 2010, PlosOne), suggesting their implication in oxidative and UV-induced stress response.

Besides their redox activities, genetic studies have shown Sestrins to be important regulators of metabolic homeostasis, mainly through the regulation of the AMPK-TORC1 axis (Lee et al, 2013, Cell Metab). Sestrins potentiate AMPK activation and thereby suppress mTORC1 activity, leading to the stimulation of cellular catabolism of sugars, proteins and lipids and upregulation of the autophagic process. At the organism level, Sestrin(s) deficiency led to defective hepatic function in mouse, fat accumulation and skeletal and cardiac muscle degeneration in *Drosophila* or reduced locomotor activity and lifespan in *C. elegans*. Studies using these animal models demonstrated that endogenous Sestrin activity was required to prevent age-associated phenotypes.

To date, no study has further investigated the expression profile, the role and function of Sestrins in healthy human skin. However, its potential application in the cosmetic industry would be of major interest.

It is thus desirable and important to provide products or active agents which prevent, reduce or even inhibit skin cell damages and ageing, and/or which can improve skin hydration, and/or which may also regulate skin pigmentation.

The Applicant has shown that SESN1, SESN2 and SESN3 genes have specific expression profiles in human epidermis and epidermal derived keratinocytes which vary with cellular differentiation status, age and UV exposure. The Applicant has shown that Sestrin deficiency in epidermal keratinocytes impacts autophagy markers expression (in the case of SESN2 deficiency) or cell differentiation markers expression (in the case of SESN3 deficiency). To its credit, the Applicant has developed an in vitro method for selecting compounds acting on Sestrin(s) expression level and which may thus be applied topically on human skin in order to improve skin condition and barrier function.

Moreover, the Applicant has shown that SESN1, SESN2 and SESN3 genes are expressed in normal human melanocytes and that their expression is modulated after UVA or UVB irradiation. Thus, compounds that regulate the expression of one of the aforesaid genes in melanocytes could impact the cell response and function towards environmental stress.

The present invention relates to an in vitro method for screening candidate compounds for preventing and/or attenuating skin ageing, and/or for hydrating the skin, comprising the following steps:
a. bringing at least one test compound in contact with a sample of human keratinocytes;
b. measuring the expression of at least one Sestrin gene chosen from SESN1, SESN2 and SESN3 in said keratinocytes;
c. selecting the compounds for which an increase of at least 1.6 fold of the expression of at least one of said genes is measured in the keratinocytes treated in a. compared with the untreated keratinocytes.

The invention also relates to an in vitro method for screening candidate compounds for regulating skin pigmentation, preferably for inhibiting skin pigmentation, comprising the following steps:
a. bringing at least one test compound in contact with a sample of human melanocytes;
b. measuring the expression of at least one Sestrin gene chosen from SESN1, SESN2 and SESN3 in said melanocytes;
c. selecting the compounds for which a significant modulation, preferably a significant increase, of the expression of at least one of said genes is measured in the melanocytes treated in a. compared with the untreated melanocytes.

According to a first embodiment, step b. is performed before and after step a. In this case, the expression of at least one Sestrin gene measured in the keratinocytes or melanocytes before step a. corresponds to the control value (i.e. untreated keratinocytes or melanocytes).

Thus, in this case, step c. comprises the selection of the compounds for which an increase of at least 1.6 fold of the expression of at least one Sestrin gene is measured in the keratinocytes treated in a. compared with the same keratinocytes before step a. In the case of melanocytes, step c. comprises the selection of the compounds for which a significant modulation, preferably a significant increase, of the expression of at least one Sestrin gene is measured in the melanocytes treated in a. compared with the same melanocytes before step a.

In one preferred embodiment, step c. comprises the selection of the compounds for which an increase of at least 2 fold of the expression of at least one Sestrin gene is measured in the keratinocytes treated in a. compared with the same keratinocytes before step a.

According to another embodiment, the method comprises a first step a'. of preparing samples of human keratinocytes or melanocytes. Thus, preferably, the present invention relates to an in vitro method for screening for candidate compounds for preventing and/or attenuating ageing of the skin, and/or for hydrating the skin, comprising the following steps:
a'. preparing at least two samples of human keratinocytes;
a. bringing one of the samples into contact with at least one test compound; then
b. measuring the expression of at least one Sestrin gene in said samples; and
c. selecting the compounds for which an increase of at least 1.6 fold of the expression of at least one of said genes is measured in the keratinocytes treated in a. as compared to the untreated keratinocytes.

In this second embodiment, the expression of at least one Sestrin gene measured in the sample of keratinocytes not submitted to step a. corresponds to the control value (i.e. untreated keratinocytes).

Preferably, the present invention also relates to an in vitro method for screening for candidate compounds regulating skin pigmentation, preferably inhibiting skin pigmentation, comprising the following steps:
 a'. preparing at least two samples of human melanocytes;
 a. bringing one of the samples into contact with at least one test compound; then
 b. measuring the expression of at least one Sestrin gene in said samples; and
 c. selecting the compounds for which a significant modulation, preferably a significant increase, of the expression of at least one of said genes is measured in the melanocytes treated in a. as compared to the untreated melanocytes.

In this second embodiment, the expression of at least one Sestrin gene measured in the sample of melanocytes not submitted to step a. corresponds to the control value (i.e. untreated melanocytes).

By "significant modulation", it is meant an increase of at least 1.6 fold or a decrease of at least 0.7 fold of the expression of at least SESN1, SESN2 or SESN3, which is notable. Preferably, it relates to an increase of at least 1.6 fold of the expression of at least SESN2 or SESN3.

By "skin ageing", it is intended any change in the external appearance of the skin due to both intrinsic ageing and photo-ageing, such as, formation of wrinkles and fine lines, loss of firmness, and also any internal change in the skin which is not systematically reflected by a changed external appearance, such as the dermic atrophy due to the decreased production and/or the degradation of collagen.

By "hydrating the skin", it is meant boosting the natural moisture of the skin by preventing the water loss and its drying, notably by improving cell differentiation and skin barrier function.

By "regulating skin pigmentation", it is meant modifying the melanin and melanosome formation and maturation, their transport, transfer, distribution and degradation in the skin.

Preferably, keratinocytes are normal human keratinocytes.

Preferably, melanocytes are normal human melanocytes.

The Sestrin gene is chosen from human SESN1, human SESN2 and human SESN3 (simply quoted "SESN1", "SESN2" or "SESN3" in the present application).

SESN1 is a human gene which may be found in the NCBI database under the Gene ID 27244, and its corresponding protein may be found in Uniprot under the accession number Q9Y6P5.

SESN2 is a human gene which may be found in the NCBI database under the Gene ID 83667, and its corresponding protein may be found in Uniprot under the accession number P58004.

SESN3 is a human gene which may be found in the NCBI database under the Gene ID 143686, and its corresponding protein may be found in Uniprot under the accession number P58005.

In this method, the measure of SESN1, SESN2 and SESN3 gene expression in step b. may be performed by real-time quantitative RT-PCR on said keratinocytes or melanocytes. However, any other means for quantifying the expression of the aforesaid genes, for instance by quantifying the production either of mRNA or protein, may be used without departing from this invention.

The test compounds may be of any type. They may be of natural origin or produced by chemical synthesis. This may involve a library of structurally defined chemical compounds, uncharacterized compounds or substances, or a mixture of compounds.

Natural compounds include compounds of chemical or vegetal origin. Preferably, the test compounds are vegetal, preferably chosen from botanical extracts. The test compounds may also be chemical products.

According to step a., the test compound is put into contact with a sample of human keratinocytes or melanocytes.

According to step b., the expression of at least one Sestrin gene is measured in said keratinocytes or melanocytes.

The term "expression of at least one Sestrin gene" is intended to mean the mRNA of the corresponding gene, or the protein encoded by the corresponding gene. Said gene expression may thus be measured by quantifying the mRNA or the protein. This is notably shown in the example.

Quantitative real time PCR classical method was used to quantify SESN gene expression. This method is based on specific hybridization of the cDNA of the genes of interest with specific nucleotide probes, their PCR-based amplification and relative quantification in real-time.

The expression of at least one Sestrin gene after treatment with the test compound is then compared to a control value, i.e. a value obtained in the same keratinocytes which are untreated.

According to step c., the useful compounds are those for which an increase of at least 1.6 fold of the expression of at least one of said genes is measured in the human keratinocytes treated in a. as compared to the untreated keratinocytes. Preferably, the activation of the expression of at least one of said genes is of at least 2 fold.

The compounds selected by means of the screening methods defined herein can subsequently be tested on other in vitro models and/or in vivo models (in humans) for their effects on skin ageing and/or skin hydration. The useful compounds according to the invention are regulators of the targeted Sestrin genes.

A subject of the invention is also the cosmetic use of a regulator, preferably an activator, of the expression of at least one Sestrin gene, which can be obtained according to the above described method, for preventing and/or attenuating skin ageing and/or for hydrating the skin and/or for regulating skin pigmentation.

Another object of the present invention is the use of at least one regulator, preferably an activator, of the expression of at least one Sestrin gene, which can be obtained according to the above described method, to make a therapeutic composition for preventing and/or attenuating skin ageing and/or for hydrating the skin and/or for regulating skin pigmentation.

The activator can be used in a proportion of from 0.001 to 10% by weight, preferably in a proportion of from 0.01 to 5% by weight of the composition.

The activator may be chosen from organic molecules (chemical products), but may also be a botanical extract.

The activators identified by the screening method described above can be formulated within a composition, in combination with a physiologically acceptable carrier, preferably a cosmetically acceptable medium, i.e. a medium that is suitable for use in contact with human skin without any risk of toxicity, incompatibility, instability or allergic response and especially that does not cause any sensations of discomfort (redness, tautness, stinging, etc.) that are unacceptable to the user. These compositions may be administered, for example, orally, or topically. Preferably, the composition is applied topically. By oral administration, the composition may be in the form of tablets, gel capsules, sugar-coated tablets, syrups, suspensions, solutions, powders, granules, emulsions, suspensions of microspheres or nanospheres or lipid or polymeric vesicles for controlled release. By topical administration, the composition is more particularly for use in treating the skin and may be in the form of salves, creams, milks, ointments, powders, impregnated pads, solutions, gels, sprays, lotions or suspensions. It may also be in the form of suspensions of microspheres or nanospheres or lipid or polymeric vesicles or polymeric patches or hydrogels for controlled release. This composition for topical application may be in anhydrous form, in aqueous form or in the form of an emulsion. The composition for topical application may be in the form of an oil-in-water, water-in-oil or multiple emulsion (W/O/W or O/W/O), which may optionally be microemulsions or nanoemulsions, or in the form of an aqueous dispersion, a solution, an aqueous gel or a powder. In a preferred variant, the composition is in the form of a gel, a cream or a lotion.

The physiologically acceptable carrier of the composition generally comprises water and optionally other solvents such as ethanol.

This composition is preferably used as a care and/or cleansing product for facial and/or bodily skin and it may especially be in the form of a fluid, a gel or a mousse, conditioned, for example, in a pump-dispenser bottle, an aerosol or a tube, or in the form of cream conditioned, for example, in a jar. As a variant, it may be in the form of a makeup product and in particular a foundation or a loose or compact powder.

It may comprise various excipients, such as at least one compound chosen from:
- oils, which may be chosen especially from: linear or cyclic, volatile or non-volatile silicone oils, such as polydimethylsiloxanes (dimethicones), polyalkylcyclosiloxanes (cyclomethicones) and polyalkylphenylsiloxanes (phenyl dimethicones); synthetic oils such as fluoro oils, alkylbenzoates and branched hydrocarbons such as polyisobutylene; plant oils and especially soybean oil or jojoba oil; and mineral oils such as liquid petroleum jelly;
- waxes such as ozokerite, polyethylene wax, beeswax or carnauba wax;
- silicone elastomers obtained especially by reaction, in the presence of a catalyst, of a polysiloxane containing at least one reactive group (especially hydrogen or vinyl) and bearing at least one alkyl group (especially methyl) or phenyl, in a terminal and/or side position, with an organosilicone such as an organohydrogenopolysiloxane;
- surfactants, preferably emulsifying surfactants, whether they are nonionic, anionic, cationic or amphoteric, and in particular fatty acid esters of polyols such as fatty acid esters of glycerol, fatty acid esters of sorbitan, fatty acid esters of polyethylene glycol and fatty acid esters of sucrose; fatty alkyl ethers of polyethylene glycol; alkylpolyglucosides; polysiloxane-modified polyethers; betaine and derivatives thereof; polyquaterniums; ethoxylated fatty alkyl sulfate salts; sulfosuccinates; sarcosinates; alkyl and dialkyl phosphates, and salts thereof; and fatty acid soaps;
- co-surfactants such as linear fatty alcohols and in particular cetyl alcohol and stearyl alcohol;
- thickeners and/or gelling agents, and in particular cross-linked or non-crosslinked, hydrophilic or amphiphilic homopolymers and copolymers, of acryloylmethylpropanesulfonic acid (AMPS) and/or of acrylamide and/or of acrylic acid and/or of acrylic acid salts or esters; xanthan gum or guar gum; cellulose derivatives; and silicone gums (dimethiconol);
- organic screening agents, such as dibenzoylmethane derivatives (including butyl-methoxydibenzoylmethane), cinnamic acid derivatives (including ethylhexyl methoxycinnamate), salicylates, para-aminobenzoic acids, $\beta,\beta'$-diphenyl acrylates, benzophenones, benzylidenecamphor derivatives, phenylbenzimidazoles, triazines, phenylbenzotriazoles and anthranilic derivatives;
- inorganic screening agents, based on mineral oxides in the form of coated or uncoated pigments or nanopigments, and in particular based on titanium dioxide or zinc oxide;
- dyes;
- preserving agents;
- sequestrants such as EDTA salts;
- fragrances;
and mixtures thereof, without this list being limiting.

Examples of such excipients are especially mentioned in the CTFA dictionary (International Cosmetic Ingredient Dictionary and Handbook published by The Cosmetic, Toiletry and Fragrance Association, 11th edition, 2006), which describes a wide variety, without limitation, of cosmetic and pharmaceutical ingredients usually used in the skincare industry, that are suitable for use as additional ingredients in the compositions according to the present invention.

The composition may also comprise at least one compound with an optical effect such as fillers, pigments, nacres, tensioning agents and matting polymers, and mixtures thereof.

The term "fillers" should be understood as meaning colorless or white, mineral or synthetic, lamellar or non-lamellar particles suitable for giving the composition body or rigidity and/or softness, a matt effect and uniformity immediately on application. Fillers that may especially be mentioned include talc, mica, silica, kaolin, Nylon® powders such as Nylon-12 (Orgasol® sold by the company Atochem), polyethylene powders, polyurethane powders, polystyrene powders, polyester powders, optionally modified starch, silicone resin microbeads such as those sold by the company Toshiba under the name Tospearl®, hydroxyapatite, and hollow silica microspheres (Silica Beads® from the company Maprecos).

The term "pigments" should be understood as meaning white or colored, mineral or organic particles that are insoluble in the medium, which are intended to color and/or opacify the composition. They may be of standard or nanometric size. Among the mineral pigments that may be mentioned are titanium dioxide, zirconium dioxide and cerium dioxide, and also zinc oxide, iron oxide and chromium oxide.

The term "nacres" should be understood as meaning iridescent particles that reflect light. Among the nacres that may be envisaged, mention may be made of natural mother-of-pearl, mica coated with titanium oxide, with iron oxide, with natural pigment or with bismuth oxychloride, and also colored titanium mica.

The mass concentration in the aqueous phase of these fillers and/or pigments and/or nacres is generally from 0.1% to 20% and preferably from 0.2% to 7% by weight relative to the total weight of the composition.

The term "tensioning agent" should be understood as meaning a compound suitable for making the skin taut and, by means of this tension effect, making the skin smooth and reducing or even immediately eliminating wrinkles and fine lines therefrom. Tensioning agents that may be mentioned include polymers of natural origin. The term "polymer of natural origin" means polymers of plant origin, polymers derived from integuments, egg proteins and latices of natural origin. These polymers are preferably hydrophilic. Polymers of plant origin that may especially be mentioned include proteins and protein hydrolyzates, and more particularly extracts of cereals, of legumes and of oil-yielding plants, such as extracts of corn, of rye, of wheat, of buckwheat, of sesame, of spelt, of pea, of bean, of lentil, of soybean and of lupin. The synthetic polymers are generally in the form of a latex or a pseudolatex and may be of polycondensate type or obtained by free-radical polymerization. Mention may be made especially of polyester/polyurethane and polyether/polyurethane dispersions. Preferably, the tensioning agent is a copolymer of PVP/dimethiconyl acrylate and of hydrophilic polyurethane (Aquamere S-2001® from the company Hydromer).

The term "matting polymers" means herein any polymer in solution, in dispersion or in the form of particles, which reduces the sheen of the skin and which unifies the complexion. Examples that may be mentioned include silicone elastomers; resin particles; and mixtures thereof. Examples of silicone elastomers that may be mentioned include the products sold under the name KSG® by the company Shin-Etsu, under the name Trefil®, BY29® or EPSX® by the company Dow Corning or under the name Gransil® by the company Grant Industries.

The composition used according to the invention may also comprise active agents other than the activator, and in particular at least one active agent chosen from: agents that stimulate the production of growth factors; anti-glycation or deglycating agents; agents that increase collagen synthesis or that prevent its degradation (anti-collagenase agents and especially matrix metalloprotease inhibitors); agents that increase elastin synthesis or prevent its degradation (anti-elastase agents); agents that stimulate the synthesis of integrin or of focal adhesion constituents such as tensin; agents that increase the synthesis of glycosaminoglycans or proteoglycans or that prevent their degradation (anti-proteoglycanase agents); agents that increase fibroblast proliferation; depigmenting or anti-pigmenting agents; antioxidants or free-radical scavengers or anti-pollution agents; and mixtures thereof, without this list being limiting.

Examples of such agents are especially: plant extracts and in particular extracts of *Chondrus crispus*, of *Therms thermophilus*, of *Pisum sativum* (Proteasyl® TP LS), of *Centella asiatica*, of *Scenedesmus*, of *Moringa pterygosperma*, of witch hazel, of *Castanea sativa*, of *Hibiscus sabdriffa*, of *Polianthes tuberosa*, of *Argania spinosa*, of *Aloe vera*, of *Narcissus tarzetta*, or of liquorice; an essential oil of *Citrus aurantium* (Neroli); α-hydroxy acids such as glycolic acid, lactic acid and citric acid, and esters thereof; β-hydroxy acids such as salicylic acid and derivatives thereof; plant protein hydrolyzates (especially of soybean or of hazelnut); acylated oligopeptides (sold especially by the company Sederma under the trade names Maxilip®, Matrixyl® 3000, Biopeptide® CL or Biopeptide® EL); yeast extracts and in particular of *Saccharomyces cerevisiae*; algal extracts and in particular of laminairia; vitamins and derivatives thereof such as retinyl palmitate, ascorbic acid, ascorbyl glucoside, magnesium or sodium ascorbyl phosphate, ascorbyl palmitate, ascorbyl tetraisopalmitate, ascorbyl sorbate, tocopherol, tocopheryl acetate and tocopheryl sorbate; arbutin; kojic acid; ellagic acid; and mixtures thereof.

As a variant or in addition, the composition used according to the invention may comprise at least one elastase inhibitor (anti-elastase), such as an extract of *Pisum sativum* seeds that is sold especially by the company Laboratoires Sérobiologiques/Cognis France under the trade name Proteasyl TP LS®.

The composition may also contain inert additives or combinations of these additives, such as wetting agents, stabilizers, moisture regulators, pH regulators, osmotic pressure modifiers, or UV-A and UV-B screens.

The following examples illustrate the invention without limiting the scope thereof.

EXAMPLE

Example 1

Test of the Expression Level of SESN1, SESN2 and SESN3 Genes in Normal Human Keratinocytes Depending on the Differentiation Status Protocol:

Normal Human Epidermal Keratinocytes (PromoCell) derived from juvenile donors were cultivated in 6-well plates in supplemented Keratinocyte Growth Medium (KGM2 basal medium+SupplementMix, Promocell) at 37° C., 5% $CO_2$. After 24 hours, cells were incubated for additional 48 hours in supplemented medium (proliferating keratinocytes) or in high calcium (1 mM) supplemented medium (differentiated keratinocytes).

Total RNA was extracted with RNeasy kit (Qiagen), according to manufacturer's instructions. The recovered RNA was quantified with Quant-iT RiboGreen RNA Assay kit (Invitrogen) and reverse transcribed using iScript Reverse Transcription SuperMix Kit (BioRad), according to the manufacturer's instructions. The cDNA generated was then subjected to quantitative real-time PCR (qRT-PCR) for the analysis of gene expression using appropriate Taqman primers corresponding to target and housekeeping genes (Applied Biosystems) and the iQ Supermix (BioRad). The reaction was carried out in a BioRad CFX96 Touch Real-Time PCR Detection System. Results were normalized relative to the expression of housekeeping genes (B2M and RPLPO). Results were expressed in terms of the fold change in expression of the target gene in the treated sample versus the untreated control sample.

Results:

Data were obtained from two donors of keratinocytes.

Evaluation of SESN1 expression level in proliferating (1.0±0.22) versus differentiated (1.53±0.09) keratinocytes shows no major variation.

Evaluation of SESN2 expression level in proliferating (1.0±0.38) versus differentiated (0.99±0.12) keratinocytes shows no variation with cell differentiation.

Evaluation of SESN3 expression in proliferating (1.0±0.16) versus differentiated (1.93±0.19) keratinocytes shows an increase in the expression of SESN3 gene with cell differentiation.

Example 2

Test of the Expression Level of SESN1, SESN2 and SESN3 Genes in Normal Human Keratinocytes After UVA/UVB Exposure Protocol:

Normal Human Epidermal Keratinocytes (PromoCell) derived from juvenile donors were cultivated in 6-well plates in supplemented Keratinocyte Growth Medium (KGM2 basal medium+SupplementMix, Promocell) at 37° C., 5% $CO_2$. At 70% confluency, cells were washed with PBS buffer (Life Technologies), then irradiated or not with UVA (10 $J/cm^2$) or UVB (20 $mJ/cm^2$) using a BioSun irradiator (Vilber Lourmat) and further incubated for 24 hours in supplemented Keratinocyte Growth Medium (Promocell).

A test similar to that of Example 1 was performed to determine Sestrin gene expression levels.

Results:

Evaluation of SESN1 expression in keratinocytes from a donor shows no major variation after UV irradiation. In untreated control keratinocytes, the relative expression level was 1.0 (±0.03), after UVA irradiation, 1.09 (±0.05) and after UVB irradiation, 1.26 (±0.08).

Evaluation of SESN2 expression in keratinocytes from a donor shows an increased expression in irradiated keratinocytes. In untreated control keratinocytes, expression level was 1.0 (±0.03), after UVA irradiation, 1.69 (±0.07) and after UVB irradiation, 1.74 (±0.11).

Evaluation of SESN3 expression in keratinocytes from a donor shows no major variation after UV irradiation. In untreated control keratinocytes, expression level was 1.0 (±0.02), after UVA irradiation, 1.01 (±0.06) and after UVB irradiation, 0.94 (±0.06).

Increasing the expression of SESN2 gene in keratinocytes thus participates in the first line of the skin defense against UV-irradiation. Therefore, compounds which stimulate the expression of SESN2 in keratinocytes should also protect against oxidative stress.

Example 3

Test of the Expression Level of SESN1, SESN2 and SESN3 Genes in Normal Human Melanocytes After UVA/UVB Exposure Protocol:

Normal Human Epidermal Melanocytes (Promocell) derived from juvenile donor were cultivated in 6-well plates in Melanocyte Growth Medium (MGM2 basal medium+ SupplementMix, PromoCell) at 37° C., 5% $CO_2$. After culturing for 48 hours, the cells were washed with PBS buffer (Life Technologies) and then irradiated or not with UVA (10 $J/cm^2$) or UVB (50 $mJ/cm^2$) using a BioSun irradiator (Vilber Lourmat) and finally incubated for 24 hours in supplemented Melanocyte Growth Medium (Promocell).

Sestrin gene expression analysis was performed as described in Example 1.

Results:

Evaluation of SESN1 expression in melanocytes from a donor shows an increased expression in UVB-irradiated melanocytes. In untreated control melanocytes, expression level was 1.0 (±0.06), after UVA irradiation, 0.77 (±0.05) and after UVB irradiation, 2.91 (±0.23).

Evaluation of SESN2 expression in melanocytes from a donor shows an increased expression in UVB-irradiated melanocytes. In untreated control melanocytes, expression level was 1.0 (±0.06), after UVA irradiation, 1.04 (±0.09) and after UVB irradiation, 4.66 (±0.18).

Evaluation of SESN3 expression in melanocytes from a donor shows a decreased expression in UVB-irradiated melanocytes. In untreated control melanocytes, expression level was 1.0 (±0.08), after UVA irradiation, 0.93 (±0.04) and after UVB irradiation, 0.16 (±0.01).

It emerges from this test that UV irradiation modulates the Sestrin genes expression by the melanocytes and thus probably impacts on melanocyte response towards environmental insults.

Example 4

Assessment of the Expression Profile of SESN1, SESN2 and SESN3 Genes in the Human Skin with Age.

Protocol:

The Distribution of Sestrin Proteins in Human Skin was Evaluated by Immunofluorescence, on Paraffin-Embedded Skin Samples from Donors of Various Age Groups.

Tissue array with sections of 4 months (4 m), 30 years (30 y), 35 years (35 y), 39 years (39 y), 49 years (49 y), 50 years (50 y) and 69 years (69 y) old female skin biopsies was used (Cybrdi). Sections were deparaffinated in xylene, rehydrated in ethanol baths, rinsed in deionised water. Antigen retrieval in 10 mM citrate buffer pH6 at 90° C. for 20 minutes was performed before blocking reaction in goat serum 3% for 1 hour. Slides were incubated overnight at 4° C. with primary antibodies: mouse pAb anti-human SESN1 (Abcam), rabbit pAb anti-human SESN2 (Sigma), rabbit pAb anti-human SESN3 (Abcam). Secondary antibodies: goat anti-mouse Alexa 488 and goat anti-rabbit Alexa 488 (Abcam) were applied 1 hour at room temperature to reveal SESNs staining. DAPI was used for nuclei staining.

Results:

Immunofluorescent staining shows that SESN1 is uniformly present in all epidermal cell layers, and that there is no major variation of SESN1 expression with age.

Concerning SESN2, there is no detectable SESN2 staining in neonatal (4 m) and aged (69 y) skin. A patchy distribution is observed in the basal layer of the epidermis of individuals between 30 and 50 years old.

SESN3 immunofluorescent staining shows an increasing gradient intensity from basal to granular layers. SESN3 is detected at all ages but varies in intensity with age: its expression is stronger in the 30-39 y old skin samples, as compared to younger (4 m) or older (69 y) skin samples.

Example 5

Assessment of the Expression Profile of SESN1, SESN2 and SESN3 Genes in Human Skin Equivalents After UVB Exposure Protocol:

The Distribution of Sestrin Proteins in UVB-Irradiated Skin Equivalents was Evaluated by Immunofluorescence on Paraffin-Embedded Skin Sections.

Human Skin Equivalents Protocol:

Keratinocytes and fibroblasts from juvenile donors were purchased from Promocell. The dermal equivalent consists of a collagen solution containing rat tail collagen type I (BD Biosciences), 10× DMEM medium (Gibco/Invitrogen), sodium bicarbonate (Gibco/Invitrogen) and fibroblasts added into 6 well-culture inserts (BD) and placed in deep 6-well culture plates (BD). After 2 hours, of polymerisation at 37° C., dermal equivalents were equilibrated in supplemented Keratinocyte Growth Medium (KGM2 basal medium+SupplementMix, Promocell) and placed at 37° C., 5% $CO_2$. After 24 hours, suspension of keratinocytes was added over the gel and submerged for 3 days in supplemented Keratinocyte Growth Medium. The inserts were placed at the air liquid interface in Serum-free Keratinocyte Defined Medium (SKDM: SKDM is a high $Ca^{2+}$ medium consisting of KGM2 basal medium, transferrin (Sigma), BSA (Sigma) and L-ascorbic acid (Sigma)) for 10 days. 24 hours before culture arrest, skin equivalents were irradiated, in duplicates, with 100 $mJ/cm^2$ UVB.

Immunofluorescence Protocol:

Human skin equivalents were fixed in 10% formalin before embedding in paraffin and cutting into 5 µm-thick sections. Sections were deparaffinized in xylene, rehydrated in ethanol baths, rinsed in deionised water. Antigen retrieval in 10 mM citrate buffer pH6 at 90° C. for 20 minutes was performed before blocking reaction in goat serum 3% for 1 hour. Slides were incubated overnight at 4° C. with the rabbit anti-human SESN2 antibody (Sigma) or the rabbit anti-human SESN3 antibody (Abcam). The secondary goat anti-rabbit Alexa 488 antibody (Abcam) was applied 1 hour at room temperature to reveal SESN2 or SESN3 staining. DAPI was used for nuclei staining.

Results:

In non-irradiated skin equivalents, SESN2 immunofluorescent staining is detected in basal keratinocytes. After UVB exposure, an increased signal intensity is observed in basal keratinocytes and SESN2-positive keratinocytes are also detected in suprabasal layers. These observations demonstrate the stimulation of the SESN2 protein expression in UVB-stressed skin equivalents.

In non-irradiated skin equivalents, SESN3 immunofluorescent staining is strongly detected in suprabasal layers, notably in granular layers. After UVB exposure, an overall decreased signal intensity is observed.

Example 6

Effect of Sestrin Gene Silencing in Cultured Keratinocytes.

Protocol:

Normal Human Epidermal Keratinocytes (PromoCell) derived from juvenile donors were transfected with a silencer RNA specific for SESN2 or SESN3 (Dharmacon) using the Nucleofector® Solution (Amaxa nucleofection kit, Lonza) according to the transfection protocol described by the supplier. Cells transfected with the siRNA to SESN2 or SESN3 and scrambled siRNA (negative control) were cultured for 48 hours in Keratinocyte Growth Medium (KGM2 basal medium+SupplementMix, Promocell) at 37° C., 5% $CO_2$.

Samples were then analyzed by quantitative real-time PCR using the same method described in Example 1 to confirm the targeted gene knockdown and also to assess its impact on the expression of autophagy (LC3) and differentiation (Loricrin) markers.

Results:

Evaluation of the expression level of the SESN2 gene in keratinocytes after silencing with siRNA to SESN2 indicates up to 79% decrease in SESN2 expression. Evaluation of the expression level of the SESN3 gene in keratinocytes after silencing with siRNA to SESN3 indicates up to 93% decrease in SESN3 expression.

The results obtained from a donor of keratinocytes show that inactivation of SESN2 expression through the specific silencer RNA decreased the LC3 gene expression level. In control keratinocytes, the expression level was 1.0 (±0.06) and in keratinocytes silenced for SESN2, the expression level was 0.55 (±0.02).

Inactivation of SESN3 expression through the specific silencer RNA decreased the Loricrin gene expression level. In control keratinocytes, the expression level was 1.0 (±0.08) and in keratinocytes silenced for SESN3, the expression level was 0.65 (±0.05).

Example 7

Test of Stimulation of the Expression of Sestrin Genes in Normal Human Keratinocytes with a Botanical Extract Protocol:

Botanical Extract 1 (*Solidago*):

*Solidago* extract is prepared as follows: the extract of *Solidago virgaurea* is obtained by extraction of crushed dried aerial parts with ethanol (or any alcoholic solvent), discoloration with activated charcoal, filtration and dilution with 1,3-propanediol (or other appropriate cosmetic solvent) so as to obtain a final extract on a liquid form.

Normal Human Epidermal Keratinocytes (PromoCell) derived from juvenile donors were cultivated in 6-well plates in supplemented Keratinocyte Growth Medium (KGM2 basal medium+SupplementMix, Promocell) at 37° C., 5% $CO_2$. At 70% confluency, cells were incubated for 24 hours with KGM2 basal medium (Promocell) containing the botanical extract tested, at various non-toxic concentrations, in triplicates. The cytotoxicity of the botanical extract was evaluated in human cultured keratinocytes before testing the activity.

Samples were then analyzed by quantitative real-time PCR using the same method described in Example 1.

Results:

The results obtained from a donor of keratinocytes are given in Table 1 below:

TABLE 1

| | Concentration | Expression level of SESN1 | Expression level of SESN2 | Expression level of SESN3 |
|---|---|---|---|---|
| Untreated control | — | 1.0 ± 0.25 | 1.0 ± 0.21 | 1.0 ± 0.25 |
| Botanical extract 1 | 0.025% | 1.74 ± 0.21 | 1.29 ± 0.20 | 2.14 ± 0.18 |

The botanical extract 1 makes it possible to stimulate the expression of SESN1 and SESN3 in normal human keratinocytes.

Example 8

Test of Stimulation of Sestrin Genes Expression in Human Skin Equivalents with a Botanical Extract 2

Protocol:

The Effect of a Botanical Extract 2 on the Expression of SESN3 Gene was Evaluated on Human Skin Equivalents by Immunofluorescence Synthetic Compound (Retinol) and Botanical Extract 2 (Fenugreek):

Fenugreek extract is prepared as follows: the extract of *Trigonella foenum-graecum* is obtained by extraction of crushed seeds with hexane, fractionation of the resulted oil using supercritical extraction process and dilution with 1,3-propanediol (or other appropriate cosmetic solvent) so as to obtain a final extract on a liquid form.

Human skin equivalents were performed as described in Example 5. Skin equivalents were placed at the air liquid interface for 10 days in serum-free keratinocyte defined medium. Botanical extract was diluted in culture medium for the last 7 days and changed by fresh dilutions every 2 days. Synthetic compound (retinol) was diluted in culture medium for the last 4 days. Each condition was done in duplicates.

Immunostaining of skin equivalents was performed as described in Example 5.

Results:

Immunofluorescence experiment reveals that the SESN3 staining intensity is decreased in skin equivalents treated with the synthetic compound retinol as compared to untreated (control) sample. Differentiation markers evaluated (Cytokeratin 10 and Loricrin) are also decreased after retinol treatment as compared to control. Inversely, SESN3 and Loricrin immunostainings are increased in skin equivalents treated with the botanical extract.

This observation, combined with those from Examples 4, 5 and 6, strongly suggests that SESN3 expression is linked to the differentiation process of keratinocytes in the epidermis.

The botanical extract 2 makes it possible to stimulate the expression of SESN3 in human skin equivalents.

Example 9

Effect of Sestrin Gene Silencing in Cultured Melanocytes—Expression Level of TYR gene Protocol:

Normal Human Epidermal Melanocytes (Invitrogen) derived from neonate donors were transfected with a silencer RNA specific for SESN1, SESN2 or SESN3 (Dharmacon) using the Lipofectamine® 3000 Reagent (Lipofectamine® 3000 Transfection Reagent, Thermo Fisher Scientific) according to the transfection protocol described by the supplier. Cells transfected with the siRNA to SESN1, SESN2 or SESN3 and scrambled siRNA (negative control) were cultured for 5 days in Melanocyte Growth Medium M2 (MGM2 basal medium+SupplementMix, Promocell) at 37° C., 5% $CO_2$.

The knockdown of the targeted genes and their impact on the expression of Tyrosinase (TYR), a key enzyme controlling the production of melanin, was then analyzed by quantitative real-time PCR using the following method.

Total RNA was extracted with RNeasy kit (Qiagen), according to manufacturer's instructions. The recovered RNA was quantified by spectrophotometry (Multiskan GO+µdrop plate, Thermo Scientific) and reverse transcribed using iScript Reverse Transcription SuperMix Kit (BioRad), according to the manufacturer's instructions. The cDNA generated was then subjected to quantitative real-time PCR (qRT-PCR) for the analysis of gene expression using appropriate Taqman primers corresponding to target and housekeeping genes (Applied Biosystems) and SsoAdvanced™ Universal Supermix (BioRad). The reaction was carried out in a BioRad CFX96 Touch Real-Time PCR Detection System. Results were normalized relative to the expression of housekeeping genes (B2M, GUSB and TBP). Results were expressed in terms of the mean fold change in expression of the target gene in the treated samples versus the untreated control samples.

Results:

Evaluation of the expression level of the SESN genes in melanocyte after silencing with specific siRNA indicates a decrease up to 74% in SESN1, 77% in SESN2 and 89% in SESN3 expression. Data were obtained from two donors of melanocytes.

The results show that inactivation of SESN1 has no major impact on the TYR gene expression level. In control melanocytes, the relative expression level was 1.0 (±0.00) and in melanocytes silenced for SESN1, the expression level was 0.98 (±0.06).

Inactivation of SESN2 increases the TYR gene expression level. In control melanocytes, the expression level was 1.0 (±0.00) and in melanocytes silenced for SESN2, the expression level was 1.40 (±0.02).

Inactivation of SESN3 increases the TYR gene expression level. In control melanocytes, the expression level was 1.0 (±0.00) and in melanocytes silenced for SESN3, the expression level was 1.39 (±0.06).

This observation suggests that SESN2 and SESN3 expression may influence the process of melanogenesis in human melanocytes.

Example 10

Cosmetic Compositions

The following compositions are prepared according to conventional methods.

The amounts of components are indicated in percentage by weight as compared to the total weight of the composition.

O/W Emulsion:

| INCI/TRADE NAME SUPPLIER | (% W/W) |
| --- | --- |
| Jojoba esters | 1-10 |
| Camellia seed oil | 1-10 |
| Butyrospermum Parkii Butter (LIPEX SHEA) | 1-10 |
| Butyrospermum parkii butter (LIPEX SHEASOFT) | 1-10 |
| Shea Butter Ethyl Esters (LIPEX SHEALIGHT) | 1-10 |
| Butyrospernum parkii butter extract (LIPEX SHEA TRIS) | 1-10 |
| Moringa oil/hydrogenated moringa oil esters & tocopherol (FLORALIPIDS MORINGA BUTTER) | 0.5-5 |
| Hydrogenated coconut oil | 0.1-7 |
| phytosteryl/octyldodecyl lauroyl glutamate (ELDEW PS-203) | 1-5 |
| cetearyl alcohol & cetearyl glucoside (MONTANOV 68 EC) | 1-5 |
| hydrogenated lecithin & C12-16 alcohols & palmitic acid (BIOPHILIC H) | 1-5 |

-continued

| INCI/TRADE NAME SUPPLIER | (% W/W) |
|---|---|
| PEG-8 BEESWAX (APIFIL CG) | 1-5 |
| polyglyceryl-6 distearate & jojoba esters 1 polyglyceryl-3 beeswax & cetyl alcohol (EMULIUM MELLIFERA) | 1-5 |
| Ammonium Acryloyldimethyltaurate/VP Copolymer (ARISTOFLEX AVC) | 1-5 |
| methyl methacrylate crosspolymer (SEPIIVIAT H 10) | 1-5 |
| silica & lauroyl lysine (AMILON) | 0.1-10 |
| methyl methacrylate crosspolymer (MAKIBEADS 150) | 0.1-10 |
| synthetic fluorphlogopite & titanium dioxide & tin oxide (HELIOS R10Y) | 1-10 |
| Sodium hyaluronate | 0.01-3 |
| Glycerin | 1-30 |
| Polyquaternium-51 | 1-10 |
| Adenosine | 0.1-0.5 |
| Niacinamide | 0.1-5 |
| Palmitoyl Tripeptide-1 & Palmitoyl Tetrapeptide-7 | 1-5 |
| Secale Cereale (Rye) Seed Extract | 1-5 |
| Ascorbyl glucoside | 0.001-5 |
| Solidago extract of example 7 | 0.001-5 |
| Glycols (Caprylyl Glycol and/or Pentylene Glycol and/or Butylene Glycol and/or propanediol) | 0.1-10 |
| Water | Qs 100 |

O/W Emulsion:

| INCI/TRADE NAME SUPPLIER | (% W/W) |
|---|---|
| Jojoba esters | 1-10 |
| Camellia seed oil | 1-10 |
| Butyrospermum Parkii Butter (LIPEX SHEA) | 1-10 |
| Butyrospermum parkii butter (LIPEX SHEASOFT) | 1-10 |
| Shea Butter Ethyl Esters (LIPEX SHEALIGHT) | 1-10 |
| Butyrospermum parkii butter extract (LIPEX SHEA TRIS) | 1-10 |
| PHYTOSQUALAN | 0.5-7 |
| cetyl dimethicone (ABIL WAX 9801) | 0.1-7 |
| isostearyl isostearate (CRODAMOL ISIS-LQ) | 1-5 |
| cetyl alcohol & glyceryl stearate & peg-75 stearate & ceteth-20 & steareth-20 (EMULIUM DELTA) | 1-5 |
| sodium polyacrylate (COVACRYL MV 60) | 1-5 |
| methyl methacrylate crosspolymer (SEPIIVIAT H 10) | 1-5 |
| silica & lauroyl lysine (AMILON) | 0.1-10 |
| methyl methacrylate crosspolymer (MAKIBEADS 150) | 0.1-10 |
| Sodium hyaluronate | 0.01-3 |
| Glycerin | 1-30 |
| Polyquaternium-51 | 1-10 |
| Adenosine | 0.1-0.5 |
| Niacinamide | 0.1-5 |
| Palmitoyl Tripeptide-1 & Palmitoyl Tetrapeptide-7 | 1-5 |
| Secale Cereale (Rye) Seed Extract | 1-5 |
| Ascorbyl glucoside | 0.001-5 |
| Fenugreek extract according to example 8 | 0.001-5 |
| Glycols (Caprylyl Glycol and/or Pentylene Glycol and/or Butylene Glycol and/or propanediol) | 0.1-10 |
| Water | Qs 100 |

The invention claimed is:

1. An in vitro method for screening candidate compounds for regulating skin pigmentation, comprising the following steps:
   a. bringing a test compound in contact with a sample of human melanocytes;
   b. measuring the expression of at least one Sestrin gene chosen from SESN3 and SESN2 in said melanocytes; and
   c. selecting said compound for regulating skin pigmentation, when an increase of at least 1.6 fold or a decrease of at least 0.7 fold of the expression of at least one of said genes is measured in the melanocytes treated in a. compared with untreated melanocytes.

2. An in vitro method for screening candidate compounds for regulating skin pigmentation, wherein said method comprises the following steps:
   a. preparing at least two samples of human melanocytes;
   b. bringing one of the samples into contact with a test compound; then
   c. measuring the expression of at least one Sestrin gene chosen from SESN3 and SESN2 in said samples; and
   d. selecting said compound for regulating skin pigmentation, when an increase of at least 1.6 fold or a decrease of at least 0.7 fold of the expression of at least one of said genes is measured in the melanocytes treated in b. as compared to the untreated melanocytes.

3. The method according to claim 1, wherein step b. is performed before and after step a.

4. The method according to claim 1, wherein the test compounds are chosen from chemical products and botanical extracts.

5. The method of claim 1, wherein the compound selected in step c. increases the expression of the at least one of said genes by at least 1.6 fold is a significant increase of expression.

* * * * *